US012622907B2

(12) United States Patent
Sinha

(10) Patent No.: US 12,622,907 B2
(45) Date of Patent: May 12, 2026

(54) HAIR LOSS THERAPY

(71) Applicant: NIRMANA BIO, INC., Dover, DE (US)

(72) Inventor: Animesh Sinha, Amherst, NY (US)

(73) Assignee: NIRMANA HEALTH, INC., Dover, DE (US)

( * ) Notice: Subject to any disclaimer, the term of this patent is extended or adjusted under 35 U.S.C. 154(b) by 317 days.

(21) Appl. No.: 18/696,459

(22) PCT Filed: Sep. 27, 2022

(86) PCT No.: PCT/US2022/044912
§ 371 (c)(1),
(2) Date: Mar. 28, 2024

(87) PCT Pub. No.: WO2023/055740
PCT Pub. Date: Apr. 6, 2023

(65) Prior Publication Data
US 2024/0374594 A1 Nov. 14, 2024

Related U.S. Application Data

(60) Provisional application No. 63/250,009, filed on Sep. 29, 2021.

(51) Int. Cl.
*A61K 9/00* (2006.01)
*A61K 31/506* (2006.01)
*A61K 31/58* (2006.01)

(52) U.S. Cl.
CPC .......... *A61K 31/506* (2013.01); *A61K 9/0053* (2013.01); *A61K 31/58* (2013.01)

(58) Field of Classification Search
CPC ..... A61K 31/506; A61K 31/58; A61K 9/0053
See application file for complete search history.

(56) References Cited

U.S. PATENT DOCUMENTS

2014/0113887 A1 4/2014 Park
2021/0283038 A1 9/2021 Sekavat

FOREIGN PATENT DOCUMENTS

AU 2011100917 A4 9/2011
IT UB20160806 A1 8/2017
KR 20220132802 A 10/2022
WO 2016065426 A1 5/2016
WO WO 2016/065426 * 5/2016 ........... A61K 31/506

OTHER PUBLICATIONS

International Application No. PCT/US2025/053095, International Search Report and Written Opinion mailed Feb. 27, 2026, 17 pages.
Chandrashekar BS et al., "Topical Minoxidil Fortified with Finasteride: An Account of Maintenance of Hair Density After Replacing Oral Finasteride," Indian Dermatology Online Journal, vol. 6, No. 1, Jan. 1, 2015.
International Search Report and Written Opinion received in PCT/US2022/044912 dated Jan. 12, 2023, pp. 9.

* cited by examiner

*Primary Examiner* — Erich A Leeser
(74) *Attorney, Agent, or Firm* — Liang & Hennessey LLP; Stanley D. Liang

(57) ABSTRACT

This disclosure relates to a single pharmaceutical composition comprising a therapeutically effective or prophylactically effective amount of both minoxidil, or a similar antihypertensive vasodilator, and a 5-alpha reductase inhibitor (in some embodiments, the 5-alpha reductase inhibitor is finasteride) for treating or preventing hair loss in a subject. This disclosure also relates to a pharmaceutical package comprising a pharmaceutical composition for oral administration of a therapeutically effective or prophylactically effective amount of minoxidil, or a similar antihypertensive vasodilator, and a pharmaceutical composition for oral administration comprising a therapeutically effective or prophylactically effective amount of a 5-alpha reductase inhibitor (in some embodiments, the 5-alpha reductase inhibitor is finasteride) for treating or preventing hair loss in a subject. The disclosure further provides methods of treating or preventing hair loss in a subject using the disclosed compositions and packages.

24 Claims, No Drawings

HAIR LOSS THERAPY

TECHNICAL FIELD

This disclosure relates to therapy for hair loss.

BACKGROUND

Hair loss (alopecia) is a loss of hair from part of the head or body of a person, though typically at least the head is involved. Hair loss can be quite severe and results in baldness. Hair loss in some people causes psychological distress. Hair loss is a common problem, especially in men, but also in women, or in any person.

SUMMARY

In one aspect, this disclosure provides a pharmaceutical package comprising two pharmaceutical compositions for oral administration to treat or prevent hair loss in a subject. The two compositions are: a pharmaceutical composition for oral administration comprising a therapeutically effective or prophylactically effective amount of minoxidil, or a similar antihypertensive vasodilator, and a pharmaceutical composition for oral administration comprising a therapeutically effective or prophylactically effective amount of a 5-alpha reductase inhibitor for treating or preventing hair loss in a subject. In some embodiments, the 5-alpha reductase inhibitor is finasteride.

In another aspect, this disclosure provides a single pharmaceutical composition for oral administration comprising a therapeutically effective or prophylactically effective amount of both minoxidil, or a similar antihypertensive vasodilator, and a 5-alpha reductase inhibitor (in some embodiments, the 5-alpha reductase inhibitor is finasteride) for treating or preventing hair loss in a subject.

In yet another aspect, this disclosure provides a method of treating or preventing hair loss in a subject in need thereof comprising administering the disclosed single composition or the disclosed compositions in the disclosed pharmaceutical package to a subject in need thereof.

Numerous other aspects are provided in accordance with these and other aspects of the invention. Other features and aspects of the present invention will become more fully apparent from the following detailed description and the appended claims.

DETAILED DESCRIPTION

As used herein, unless otherwise indicated, the word "a" or "plurality" before a noun represents one or more of the particular noun.

The term "a single pharmaceutical composition" does not represent more than one composition.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

"Effective amount," "prophylactically effective amount," or "therapeutically effective amount" refers to an amount of an agent or composition that provides a beneficial effect or favorable result to a subject, or alternatively, an amount of an agent or composition that exhibits the desired in vivo or in vitro activity. "Effective amount," "prophylactically effective amount," or "therapeutically effective amount" refers to an amount of an agent or composition that provides the desired biological, therapeutic, and/or prophylactic result. That result can be reduction, amelioration, palliation, lessening, delaying, and/or alleviation of one or more of the signs, symptoms, or causes of a disease, disorder or condition in a patient/subject, or any other desired alteration of a biological system. "Effective amount," "prophylactically effective amount," or "therapeutically effective amount" can be an amount administered as more than one dose of a formulation/composition.

In cases where more than one drug is administered to a subject, "effective amount," "prophylactically effective amount," or "therapeutically effective amount" refers to an amount of one of the drugs that either is effective, prophylactically effective, or therapeutically effective by itself or in combination with an amount of the other drug(s).

As used herein, a "patient" and a "subject" are interchangeable terms and may refer to a human patient/subject, a non-human primate, etc.

All ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" or "5 to 10" or "5-10" should be considered to include the end points 5 and 10.

It is further to be understood that the feature or features of one embodiment may generally be applied to other embodiments, even though not specifically described or illustrated in such other embodiments, unless expressly prohibited by this disclosure or the nature of the relevant embodiments. Likewise, compositions and methods described herein can include any combination of features and/or steps described herein not inconsistent with the objectives of the present disclosure. Numerous modifications and/or adaptations of the compositions and methods described herein will be readily apparent to those skilled in the art without departing from the present subject matter.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

HAIR LOSS

Hair loss (alopecia) is a loss of hair from part of the head or body, though typically at least the head is involved. Hair loss can be quite severe and results in baldness. Hair loss in some people causes psychological distress. Hair loss is a common problem, especially in men, but also in women.

Finasteride ($C_{23}H_{36}N_2O_2$) is usually prescribed as a 1 mg pill for oral administration to treat hair loss in a subject, but a topical formulation does exist although not commonly used.

Results of phase III clinical studies in 1,879 men have shown that oral finasteride at 1 mg/day promotes hair growth and prevents further hair loss in a significant proportion of men with male pattern hair loss. Evidence suggests that the improvement in hair count reported after 1 year is maintained during 2 years of treatment. In men with vertex hair loss, global photographs showed improvement in hair growth in 48% of finasteride recipients at 1 year and in 66% at 2 years compared with 7% of placebo recipients at each time point. Furthermore, hair counts in these men showed that 83% of finasteride versus 28% of placebo recipients had no further hair loss compared with baseline after 2 years.

Minoxidil ($C_9H_{15}N_5O$) is relatively successful for hair treatment, applied topically on to scalp of a subject/patient as a scalp tonic or foam. This is the preferred and first choice of minoxidil treatment as topical minoxidil products are well established for their safety and effectiveness.

There are certain circumstances that minoxidil can be taken orally as a tablet. Oral minoxidil can be considered for hair loss especially if: topical minoxidil preparations cause a rash, irritation, or allergy; there is a lack of any benefit from topical minoxidil after 6 months of diligent use; topical minoxidil causes poor hair texture-sometimes minoxidil can cause dry, tangled hair that is prone to breakage; and other difficulties using topical minoxidil, causing compliance problems.

Oral minoxidil is mainly used for male and female pattern hair loss. However, there can be benefit with other types of hair loss too including telogen effluvium, traction alopecia and loose anagen syndrome.

The studies with oral minoxidil are very small but indicate that about one third of patients will notice a reduction in shedding, and a third will notice improved growth in 6 months or more. This means that up to 2 in 3 people out of 10 will benefit from oral minoxidil at 6 months. It is best to take treatment for 6 to 12 months to give it enough time to work.

The only head to head study comparing oral minoxidil to topical minoxidil in women with Female Pattern Hair Loss showed that 1 mg of minoxidil gave comparable effects to 5% solution (1 ml) once a day. Ramos, P. M. et al., *J Am Acad Dermatol* 2020; 82:252-253. In this study, 26 women received oral minoxidil and 26 women received topical minoxidil. After 24 weeks of treatment, there was a 12% increase in hair density for women on oral minoxidil and 7.2% increase for women applying topical minoxidil. The difference was not statistically significant but the oral minoxidil group also had less hair shedding.

Minoxidil is available in 2.5 mg, 5 mg and 10 mg tablets. A common starting dose is 0.625 mg per day. The optimum dose for hair loss is not entirely clear. It may be in the region of 0.625 mg to 2.5 mg per day. For men, a slightly higher dose may sometimes be required.

Doses of minoxidil for hair loss are considered 'low dose'. This is because the doses used for hair loss are a lot lower than the doses which are used for conditions such as hypertension. The doses used for hypertension are 10-40 mg per day.

Side effects are very uncommon at the low doses which are used to treat hair loss. The largest study looking at side effects (Vañó-Galván S. et al., *J Am Acad Dermatol* 2021; 84:1644-1651) showed that in 943 women and 461 men, 2.5% of women and 0.5% of men had to stop treatment because of a side effect.

METHODS AND COMPOSITIONS

In one aspect, this disclosure provides a pharmaceutical package comprising two pharmaceutical compositions for oral administration to a subject to treat or prevent hair loss: a pharmaceutical composition for oral administration of a therapeutically effective or prophylactically effective amount of minoxidil, or a similar antihypertensive vasodilator, and a pharmaceutical composition for oral administration comprising a therapeutically effective or prophylactically effective amount of a 5-alpha reductase inhibitor, for treating or preventing hair loss in a subject. In some embodiments, the 5-alpha reductase inhibitor is finasteride. In some embodiments, the package comprises a pharmaceutical composition for oral administration of a therapeutically effective or prophylactically effective amount of minoxidil.

The pharmaceutical package is any suitable package. In some embodiments, the pharmaceutical package is a blister pack.

By having both drugs in a package, the disclosed package allows for greater patient compliance and patient convenience, and less mistake in taking the medicines.

In some embodiments, the package carries either the pharmaceutical composition for oral administration of a therapeutically effective or prophylactically effective amount of minoxidil, or a similar antihypertensive vasodilator, or the pharmaceutical composition for oral administration comprising a therapeutically effective or prophylactically effective amount of a 5-alpha reductase inhibitor (in some embodiments, the 5-alpha reductase inhibitor is finasteride) in liquid form. In yet other embodiments, the package carries both the pharmaceutical composition for oral administration of a therapeutically effective or prophylactically effective amount of minoxidil, or a similar antihypertensive vasodilator, and the pharmaceutical composition for oral administration comprising a therapeutically effective or prophylactically effective amount and a 5-alpha reductase inhibitor (in some embodiments, the 5-alpha reductase inhibitor is finasteride) in liquid form.

In another aspect, the two compositions, one comprising minoxidil, or a similar antihypertensive vasodilator, and another comprising a 5-alpha reductase inhibitor (in some embodiments, the 5-alpha reductase inhibitor is finasteride) are in liquid form in a disclosed pharmaceutical package. In some embodiments, the two compositions are mixed together shortly before been administered to the subject. In some embodiments, the two compositions are mixed together immediately before administration. In other embodiments, the two compositions are mixed together within a day before administration. Any person can mix the two compositions together, including, without limitation, the subject, a caregiver for the subject, and a pharmacist or another person at the pharmacy.

Liquid form includes, without limitation, liquid (a solution), semi-liquid and suspension. The liquid form is in any suitable liquid, semi-liquid or suspension.

In another aspect, this disclosure relates to a method of treating or preventing hair loss in a subject in need thereof comprising administering by oral administration a pharmaceutical composition comprising a therapeutically effective or prophylactically effective amount of minoxidil, or a similar antihypertensive vasodilator, and a 5-alpha reductase inhibitor (in some embodiments, the 5-alpha reductase inhibitor is finasteride) to the subject. In some embodiments, the composition is a disclosed single pharmaceutical composition comprising both minoxidil, or a similar antihypertensive vasodilator, and a 5-alpha reductase inhibitor (in some embodiments, the 5-alpha reductase inhibitor is finasteride). In some embodiments, the compositions are contained in the disclosed pharmaceutical package. In some embodiments, the method further comprises administering to the subject by topical administration a topical pharmaceutical composition comprising a therapeutically effective or prophylactically effective amount of minoxidil, or a similar antihypertensive vasodilator, and/or a topical composition comprising a therapeutically effective or prophylactically effective amount of a 5-alpha reductase inhibitor (in some embodiments, the 5-alpha reductase inhibitor is finasteride).

5α-Reductase inhibitors, also known as dihydrotestosterone blockers, inhibit the enzyme 5α-reductase. Any suitable 5α-Reductase inhibitor is included in the disclosed compositions, packages, and used in the methods. 5α-Reductase inhibitors include, without limitation, finasteride, epristeride, dutasteride, alfatradiol. In some embodiments, the 5-alpha reductase inhibitor is finasteride.

A similar antihypertensive vasodilator to minoxidil includes, without limitation, hydralazine, nitroglycerin, losartan, diltiazem, benazepril, lisinopril. Minoxidil is a direct vasodilator, thus a similar antihypertensive vasodilator to minoxidil includes any and all direct vasodilator, including, without limitation, hydralazine, sodium nitroprusside.

The subject is any subject, including a male subject and a female subject.

In some embodiments, the disclosed composition for oral administration comprises about 0.2 to about 5 mg of finasteride; in further embodiments, the disclosed composition for oral administration comprises about 1 to about 3 mg finasteride. In some embodiments, the disclosed composition for oral administration comprises about 1 or about 3 mg finasteride.

In some embodiments, the disclosed composition for oral administration comprises about 0.625 to about 10 mg minoxidil. In further embodiments, the disclosed composition for oral administration comprises about 0.625 mg, about 2.5 mg, about 5 mg minoxidil, or about 10 mg minoxidil.

In some embodiments, the disclosed composition for oral administration comprises about 1 or about 3 mg finasteride and about 0.625 to about 5 mg minoxidil. In further embodiments, the disclosed composition for oral administration comprises about 1 mg or about 3 mg finasteride and about 0.625 mg, about 2.5 mg, about 5 mg or about 10 mg minoxidil.

FORMULATING AND ADMINISTERING COMPOSITIONS

The disclosed composition may be administered to a subject in need thereof at any suitable frequency, and at any suitable, effective dosage.

The disclosed single composition is for oral administration and is provided in a form suitable for oral administration, such as a tablet, pill, lozenge, capsule, liquid suspension, liquid solution, or any other conventional oral dosage form. The oral dosage forms may provide immediate release, delayed release, sustained release, or enteric release, and, if appropriate, comprise one or more coating. The composition can be in any suitable form, such as solid or liquid.

The disclosed package contains compositions for oral administration and the compositions are provided in a form suitable for oral administration, such as a tablet, pill, lozenge, capsule, liquid suspension, liquid solution, or any other conventional oral dosage form. The oral dosage forms may provide immediate release, delayed release, sustained release, or enteric release, and, if appropriate, comprise one or more coating.

The topical composition is for topical administration and is provided in a form suitable for topical administration, such as a gel, foam, solution, or any other conventional topical formulation.

The composition can be produced by methods employed in accordance with general practice in the pharmaceutical industry, such as, for example, the methods illustrated in *Remington: The Science and Practice of Pharmacy* (Pharmaceutical Press; 21st revised ed. (2011) (hereinafter "*Remington*").

In some embodiments, the composition comprises at least one pharmaceutically acceptable vehicle or excipient. These include, for example, diluents, carriers, excipients, fillers, disintegrants, solubilizing agents, dispersing agents, preservatives, wetting agents, preservatives, stabilizers, buffering agents (e.g. phosphate, citrate, acetate, tartrate), suspending agents, emulsifiers, and penetration enhancing agents such as DMSO, as appropriate. The composition can also comprise suitable auxiliary substances, for example, solubilizing agents, dispersing agents, suspending agents and emulsifiers.

In certain embodiments, the composition further comprises suitable diluents, glidants, lubricants, acidulants, stabilizers, fillers, binders, plasticizers or release aids and other pharmaceutically acceptable excipients.

A complete description of pharmaceutically acceptable excipients can be found, for example, in *Remington's Pharmaceutical Sciences* (Mack Pub., Co., N.J. 1991) or other standard pharmaceutical science texts, such as the *Handbook of Pharmaceutical Excipients* (Shesky et al. eds., 8th ed. 2017).

Large macromolecules that are slowly metabolized, such as proteins, polysaccharides, polylactic acids, polyglycolic acids, polymeric amino acids, copolymers of amino acids, can also be used as carrier compounds for the composition. Pharmaceutically acceptable carriers in therapeutic compositions may additionally contain liquids, such as water, saline, glycerol or ethanol. Moreover, the said compositions may further comprise excipients, such as wetting agents or emulsifiers, buffering substances, and the like. Such excipients include, among others, diluents and carriers conventional in the art, and/or substances that promote penetration of the active compound into the cell, for example, DMSO, as well as preservatives and stabilizers.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

What is claimed is:

1. A pharmaceutical package for treating or preventing hair loss in a subject comprising a pharmaceutical composition for oral administration of a therapeutically effective or prophylactically effective amount of minoxidil, or a similar antihypertensive vasodilator, and a pharmaceutical composition for oral administration comprising a therapeutically effective or prophylactically effective amount of a 5-alpha reductase inhibitor.

2. The pharmaceutical package of claim 1, wherein the package comprises a pharmaceutical composition for oral administration of a therapeutically effective or prophylactically effective amount of minoxidil.

3. The pharmaceutical package of claim 2, wherein the 5-alpha reductase inhibitor is finasteride.

4. The pharmaceutical package of claim 3, wherein the pharmaceutical package is a blister pack.

5. The pharmaceutical package of claim 3, wherein either the pharmaceutical composition comprising minoxidil, or the pharmaceutical composition comprising finasteride is in liquid form.

6. The pharmaceutical package of claim 3, wherein both the pharmaceutical composition comprising minoxidil, or the pharmaceutical composition comprising finasteride are in liquid form.

7. The pharmaceutical package of claim 3, wherein the composition comprising finasteride comprises 1.5 mg to 5 mg finasteride.

8. The pharmaceutical package of claim 3, wherein the composition comprising minoxidil comprises 5 mg to 10 mg minoxidil.

9. The pharmaceutical package of claim 3, wherein the composition comprising minoxidil comprises 5 mg minoxidil or 10 mg minoxidil.

10. A single pharmaceutical composition for oral administration comprising a therapeutically effective or prophylactically effective amount of minoxidil, or a similar antihypertensive vasodilator, and 1.5 mg to 5 mg finasteride for treating or preventing hair loss in a subject.

11. The single composition of claim 10 comprising a therapeutically effective or prophylactically effective amount of minoxidil and 1.5 mg to 5 mg finasteride for treating or preventing hair loss in a subject.

12. The single composition of claim 11, wherein the composition comprising minoxidil comprises 5 mg to 10 mg minoxidil.

13. The single composition of claim 11, wherein the composition comprising minoxidil comprises 5 mg minoxidil or 10 mg minoxidil.

14. The single composition of claim 11, wherein the single composition results from mixing two pharmaceutical compositions in liquid form, a first pharmaceutical composition and a second pharmaceutical composition, together shortly before being administered to the subject, wherein the two compositions are contained in a pharmaceutical package for treating or preventing hair loss in the subject, said package comprising the first pharmaceutical composition for oral administration of a therapeutically effective or prophylactically effective amount of minoxidil, and the second pharmaceutical composition for oral administration comprising a therapeutically effective or prophylactically effective amount of 1.5 mg to 5 mg finasteride; wherein the pharmaceutical package is a blister pack.

15. The single composition of claim 11, wherein the pharmaceutical package is a blister pack.

16. A method of treating or preventing hair loss in a subject in need thereof comprising administering by oral administration a single pharmaceutical composition of claim 11 to said subject.

17. The method of claim 16, wherein the subject is male.

18. A method of treating or preventing hair loss in a subject in need thereof comprising administering to said subject by oral administration a first pharmaceutical composition of a therapeutically effective or prophylactically effective amount of minoxidil, or a similar antihypertensive vasodilator, and a second pharmaceutical composition for oral administration comprising a therapeutically effective or prophylactically effective amount of a 5-alpha reductase inhibitor, wherein the first pharmaceutical composition and the second pharmaceutical composition are contained in a pharmaceutical package of claim 2.

19. The method of claim 18, wherein the first pharmaceutical composition comprises a therapeutically effective or prophylactically effective amount of minoxidil.

20. The method of claim 18, wherein the 5-alpha reductase inhibitor is finasteride.

21. The method of claim 18, wherein the subject is male.

22. The method of claim 18, further comprising administering to the subject by topical administration a first topical pharmaceutical composition comprising a therapeutically effective or prophylactically effective amount of minoxidil, or a similar antihypertensive vasodilator, and/or a second topical pharmaceutical composition comprising a therapeutically effective or prophylactically effective amount of a 5-alpha reductase inhibitor.

23. The method of claims 22, wherein the 5-alpha reductase inhibitor is finasteride.

24. The method of claim 22, wherein the first topical pharmaceutical composition comprises a therapeutically effective or prophylactically effective amount of minoxidil.

* * * * *